(12) United States Patent
Malkut

(10) Patent No.: US 11,497,446 B2
(45) Date of Patent: Nov. 15, 2022

(54) SYSTEMS AND METHODS FOR ANIMAL PATIENT HEALTH MANAGEMENT DURING VETERINARY PROCEDURES

(71) Applicant: Colorado State University Research Foundation, Fort Collins, CO (US)

(72) Inventor: Natalie M. Malkut, Loveland, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 711 days.

(21) Appl. No.: 16/547,338

(22) Filed: Aug. 21, 2019

(65) Prior Publication Data

US 2020/0060616 A1 Feb. 27, 2020

Related U.S. Application Data

(60) Provisional application No. 62/721,292, filed on Aug. 22, 2018.

(51) Int. Cl.
| | |
|---|---|
| *A61B 5/01* | (2006.01) |
| *A61D 99/00* | (2006.01) |
| *A61B 5/00* | (2006.01) |
| *A61B 8/08* | (2006.01) |
| *A61D 9/00* | (2006.01) |
| *A61D 3/00* | (2006.01) |

(52) U.S. Cl.
CPC .......... *A61B 5/6829* (2013.01); *A61B 5/0008* (2013.01); *A61B 5/01* (2013.01); *A61B 5/6831* (2013.01); *A61B 8/488* (2013.01); *A61D 9/00* (2013.01); *A61D 99/00* (2013.01); *A61B 2560/0468* (2013.01); *A61B 2562/16* (2013.01); *A61D 2003/006* (2013.01)

(58) Field of Classification Search
None
See application file for complete search history.

(56) References Cited

U.S. PATENT DOCUMENTS

| | | | |
|---|---|---|---|
| 8,369,924 B1* | 2/2013 | Chang | A61B 5/282 600/509 |
| 2019/0159728 A1* | 5/2019 | Pritchard | A61B 8/4209 |
| 2020/0163602 A1* | 5/2020 | Pareddy | A61B 5/6807 |

* cited by examiner

*Primary Examiner* — Jon Eric C Morales
(74) *Attorney, Agent, or Firm* — Polsinelli PC

(57) ABSTRACT

Implementations described and claimed herein provide systems and methods for managing animal patient during a veterinary procedure. In one implementation, a base has an interior surface, an exterior surface, and an opening. An electrode is disposed in the opening. The electrode is configured to communicate with medical device(s) for monitoring vital(s) of the patient during the procedure. A thermal insulator extends from the base. The thermal insulator forms a housing. An internal cavity is defined within the housing. The foot of the patient is receivable into the internal cavity. The thermal insulator regulates the body temperature of the animal patient during the veterinary procedure by retaining heat within the internal cavity.

20 Claims, 12 Drawing Sheets

SYSTEMS AND METHODS FOR ANIMAL PATIENT HEALTH MANAGEMENT DURING VETERINARY PROCEDURES

CROSS-REFERENCE TO RELATED APPLICATIONS

The present application claims priority to U.S. Provisional Application No. 62/721,292, entitled "System and Methods for Animal Patient Health Management during Veterinary Procedures" and filed on Aug. 22, 2018, which is incorporated by reference in its entirety herein.

FIELD

Aspects of the present disclosure relate generally to body temperature regulation of an animal patient and more particularly to systems and methods for regulating a body temperature of an animal patient during a veterinary procedure while facilitating monitoring of vitals of the animal patient.

BACKGROUND

Regulation of body temperature of an animal patient while under anesthesia may be critical to a positive outcome of a veterinary procedure. More particularly, while an animal patient is under anesthesia, the patient may not be able to effectively regulate its own body temperature, which may lead to adverse medical conditions such as hypothermia. One of the areas through which heat predominately escapes for many animal patients is the paws. However, while the animal patient is under anesthesia, vitals of the patient are typically monitored using the paws. As such, the paws conventionally remain exposed with one or more monitoring devices connected to the animal patient with tape. Accordingly, not only is heat escaping through the paws during the procedure, thereby potentially causing adverse health conditions, the tape creates a mess, rips the hair/fur off the patient when removed, irritates the skin of the patient, and/or otherwise causes problems during use or after removal. It is with these observations in mind, among others, that various aspects of the present disclosure were conceived and developed.

SUMMARY

Implementations described and claimed herein address the foregoing problems by providing systems and methods for managing an animal patient during a veterinary procedure. In one implementation, a base has an interior surface and an exterior surface. A thermal insulator extends from the base, and the thermal insulator forms a housing with the base. A strap set has one or more straps extending from a first side of the housing to a second side of the housing. The strap set is adapted to apply a tension against a foot of the animal patient, and the tension is adjustable using the strap set. An opening is defined in the base. An electrode is disposed in the opening. The electrode is configured to capture one or more vitals of the animal patient during the veterinary procedure and to communicate the one or more vitals to at least one medical device for monitoring of the animal patient. An internal cavity is defined within the housing. The foot of the animal patient is receivable into the internal cavity. The thermal insulator regulates the body temperature of the animal patient during the veterinary procedure by retaining heat within the internal cavity.

In another implementation, a housing is formed from a thermal insulator and a base. The housing is held in tension against a foot of an animal patient. An opening is defined in the base. An internal cavity is defined within the housing. The foot of the animal patient is receivable into the internal cavity. The thermal insulator regulates the body temperature of the animal patient during the veterinary procedure by retaining heat within the internal cavity. A sensor is disposed in the opening, and the sensor is configured to capture one or more vitals of the animal patient from the foot during the veterinary procedure.

In another implementation, a monitoring component is received on an interior surface of a base relative to an opening defined in the base. An electrode is received in the opening defined in the base. A foot of an animal patient is received in an internal cavity of a housing formed by a thermal insulator connected to the base. The monitoring component is oriented between a portion of the foot and the electrode using the housing. The electrode captures one or more vitals of the animal patient from the foot during the veterinary procedure. A thermal environment is generated within the internal cavity. A body temperature of the animal patient is regulated during the veterinary procedure using the thermal environment.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

DETAILED DESCRIPTION

Aspects of the presently disclosed technology relate to systems and methods for regulating a body temperature of a paw of an animal patient during a veterinary procedure. Generally, each paw of an animal patient may be inserted into a boot for wearing while under anesthesia during a veterinary procedure. The boot retains the body heat of the paw to maintain and otherwise regulate the body temperature of the animal patient during the procedure, while also providing access to the paw for monitoring one or more vitals of the animal patient. In one aspect, the boot includes a thermal insulator extending from a base. The thermal insulator forms a housing with an internal cavity defined within the housing. The paw of the animal patient is insertable into the internal cavity, and the thermal insulator retains the body temperature of the paw within the internal cavity, thereby providing a resistance to heat dissipation via the paws. The housing is held in tension against the paw of the animal patient to provide a snug fit. For example, tension may be applied against the paw using a strap set having one or more straps. The straps may be removable, adjustable, detachable, and/or the like. Access to the paws of the patient for vitals monitoring may be provided via one or more electrodes disposed in the base. Other features and advantages will be apparent from the present disclosure.

Figure 1:
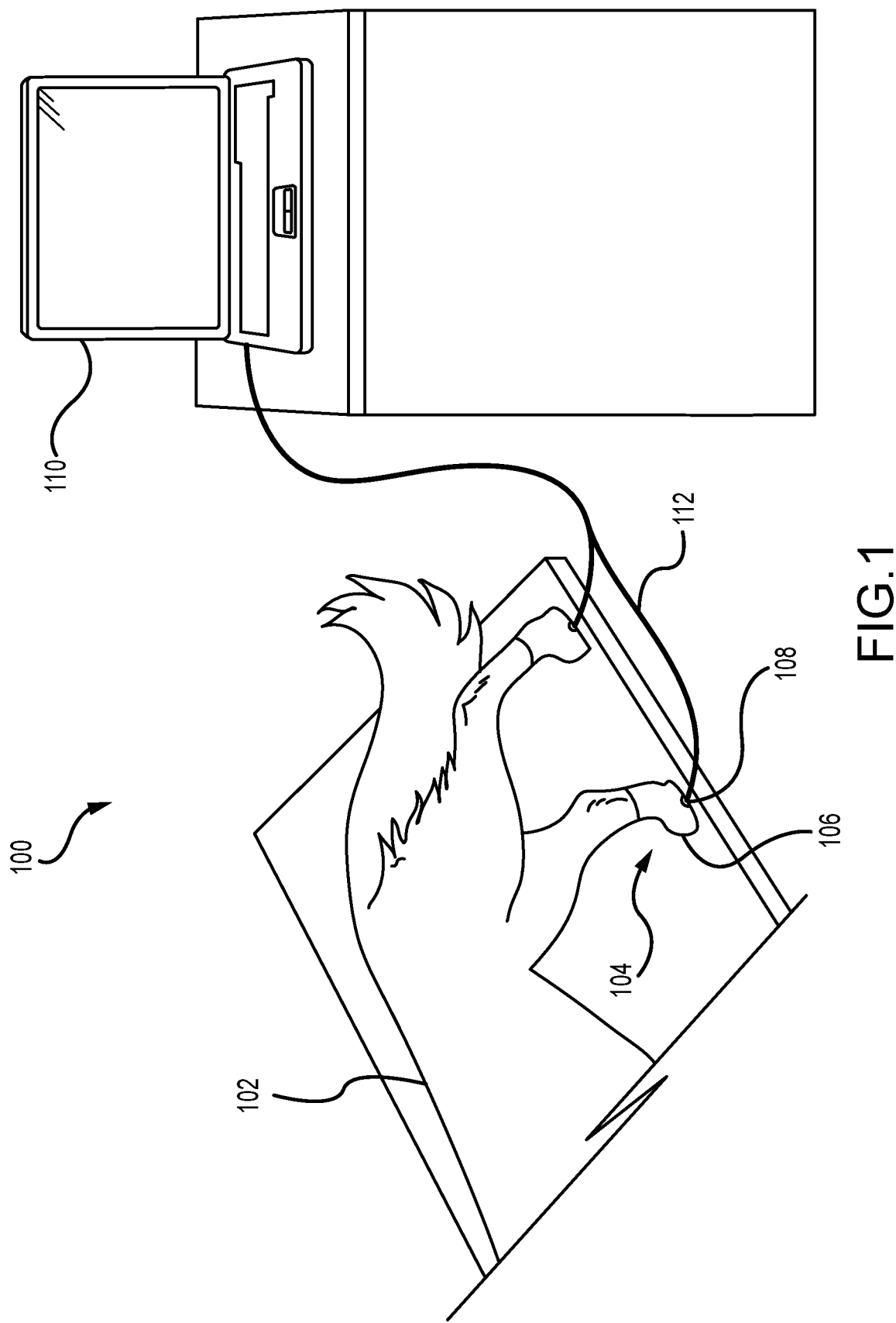
FIG. 1 illustrates an example system including a boot for regulating a body temperature and monitoring vitals of an animal patient while under anesthesia during a veterinary procedure.
Figure 2:
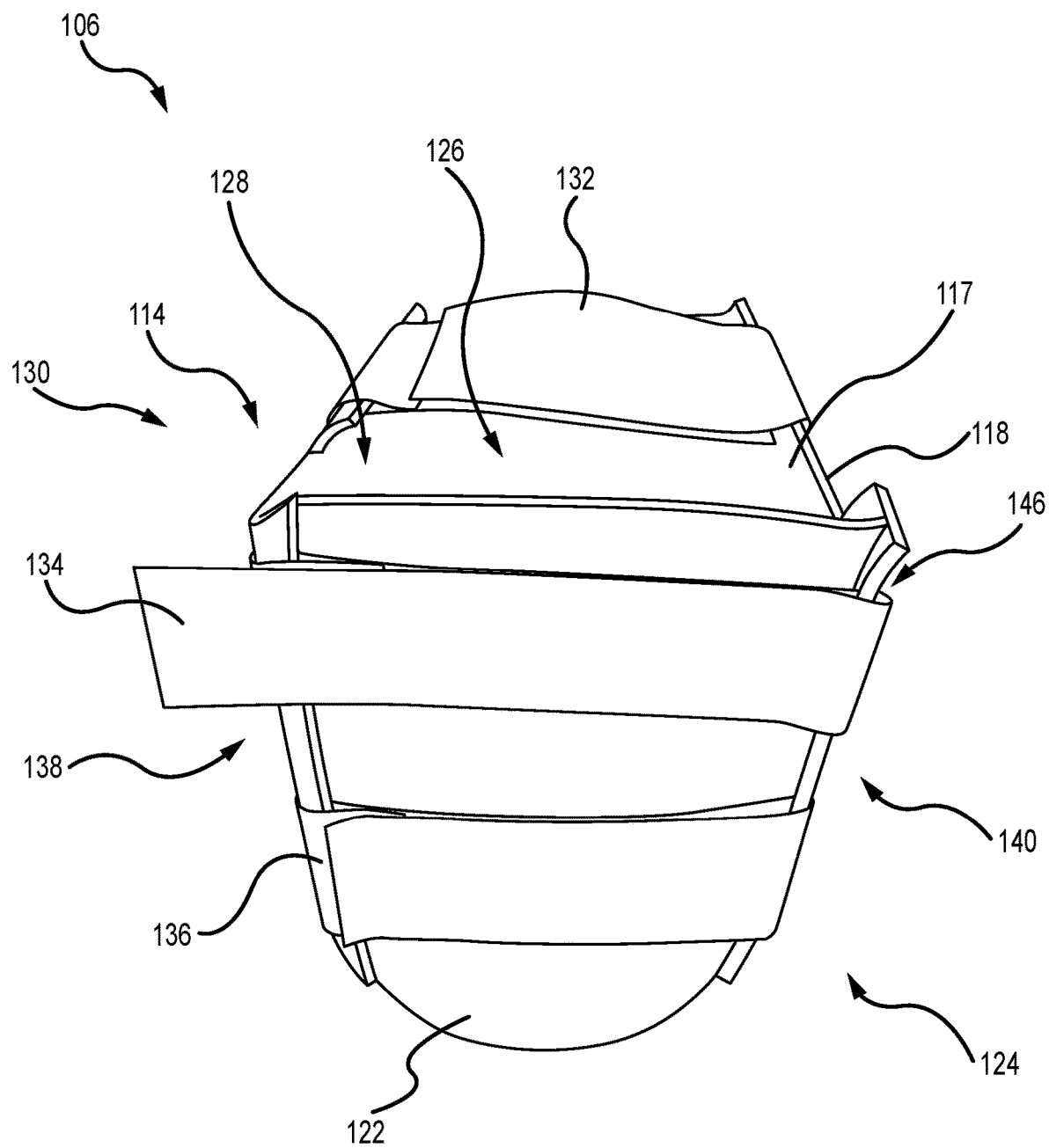
FIGS. 2-3 illustrate a front view of an example of the boot with straps secured and unsecured, respectively.
Figure 3:
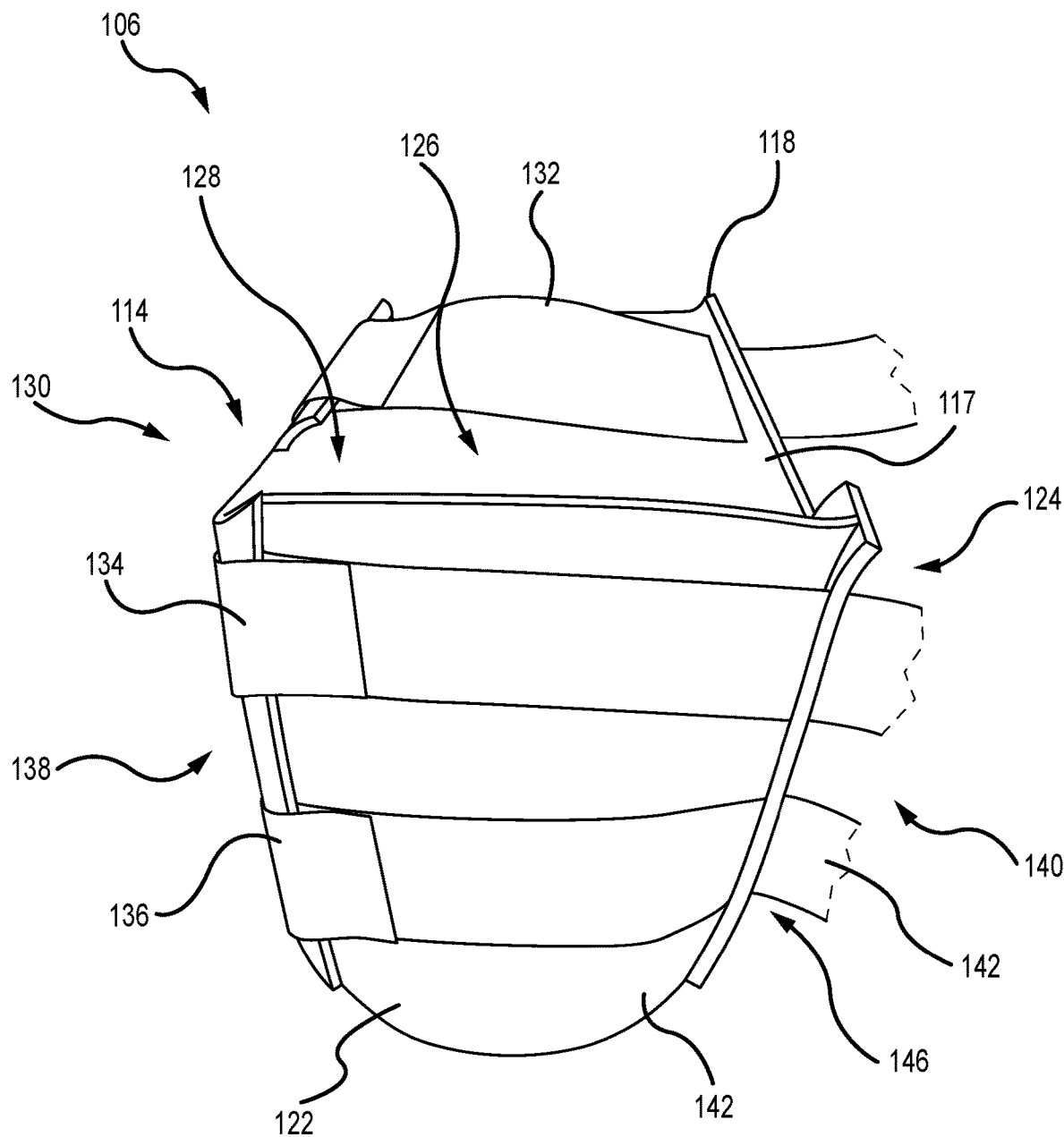
Figure 4:
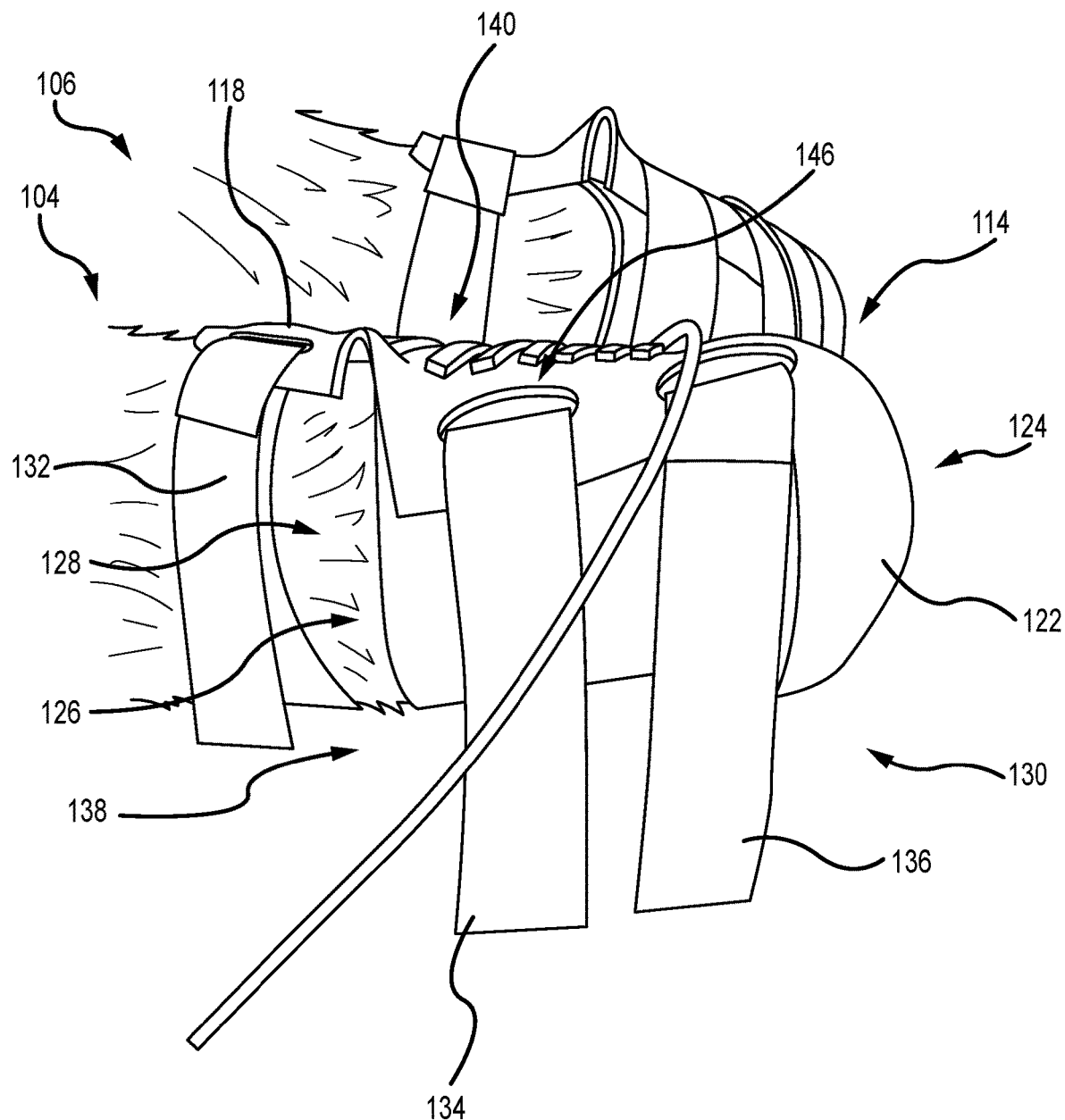
FIG. 4 depicts a perspective front view of the boot worn by an example canine patient during a veterinary procedure.
Figure 5:
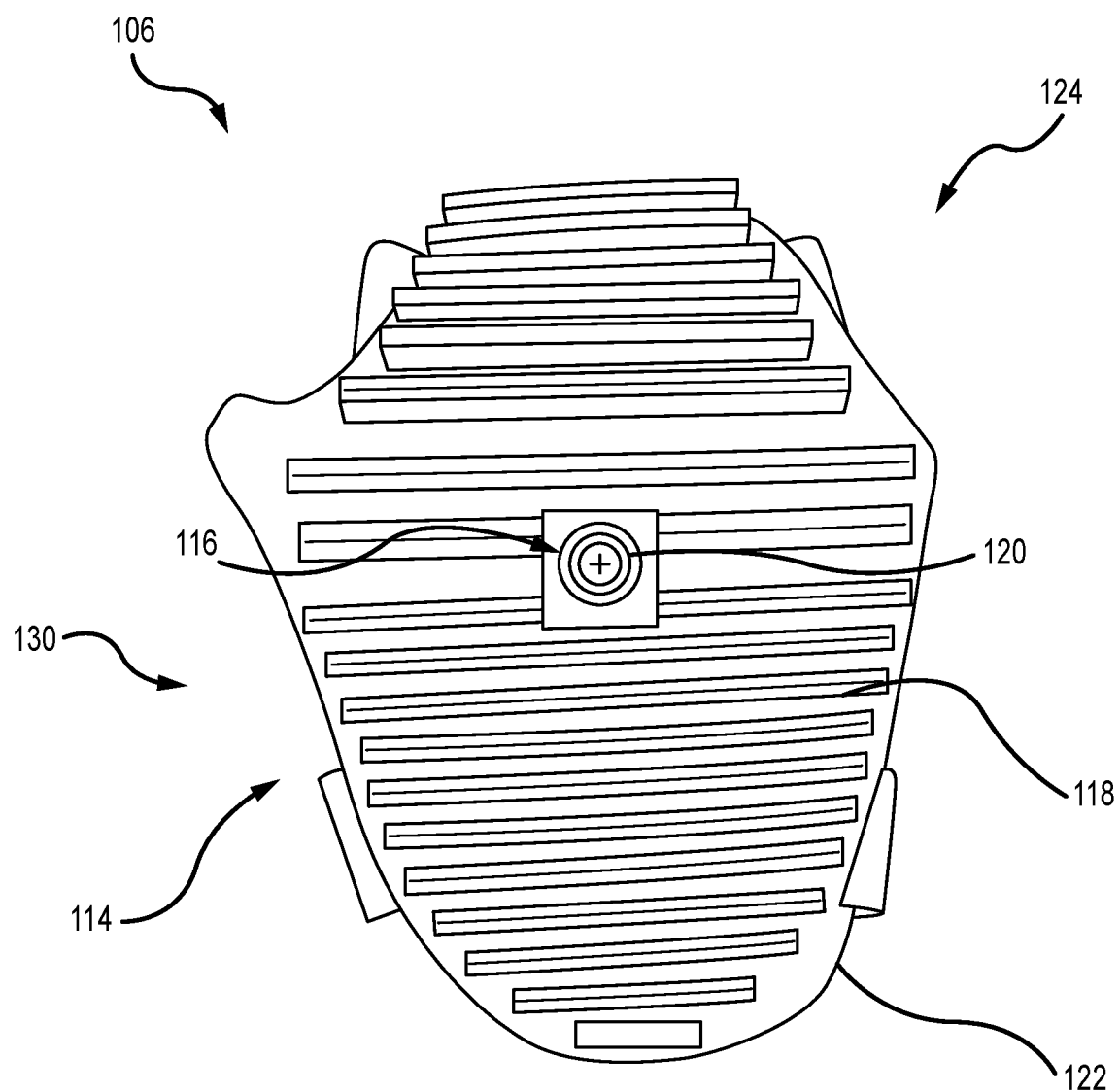
FIG. 5 shows a back view of the boot.
Figure 6:
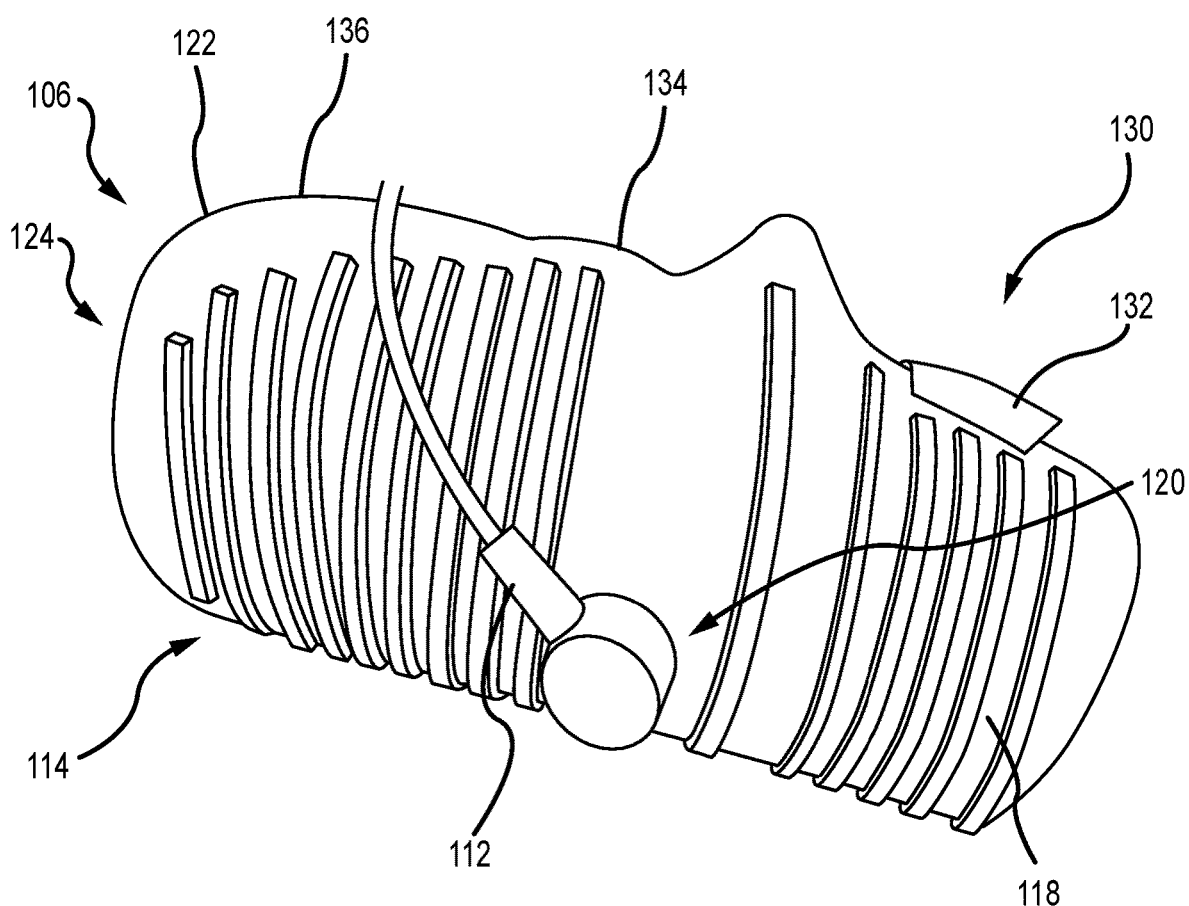
FIG. 6 illustrates a back perspective view of the boot worn by an example canine patient during a veterinary procedure.
Figure 7A:
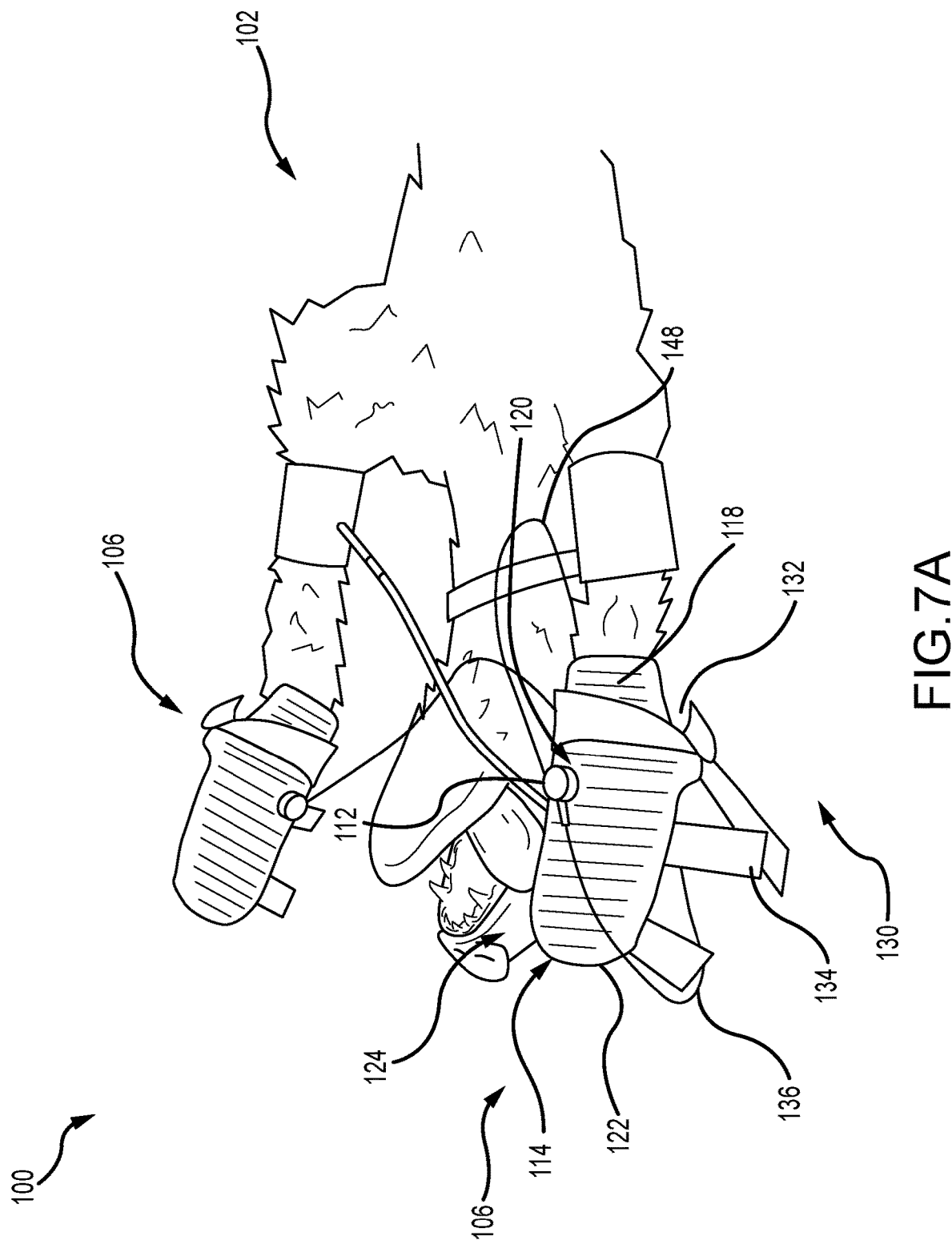
FIG. 7A shows an example canine patient wearing a set of the boots during a veterinary procedure.
Figure 7B:
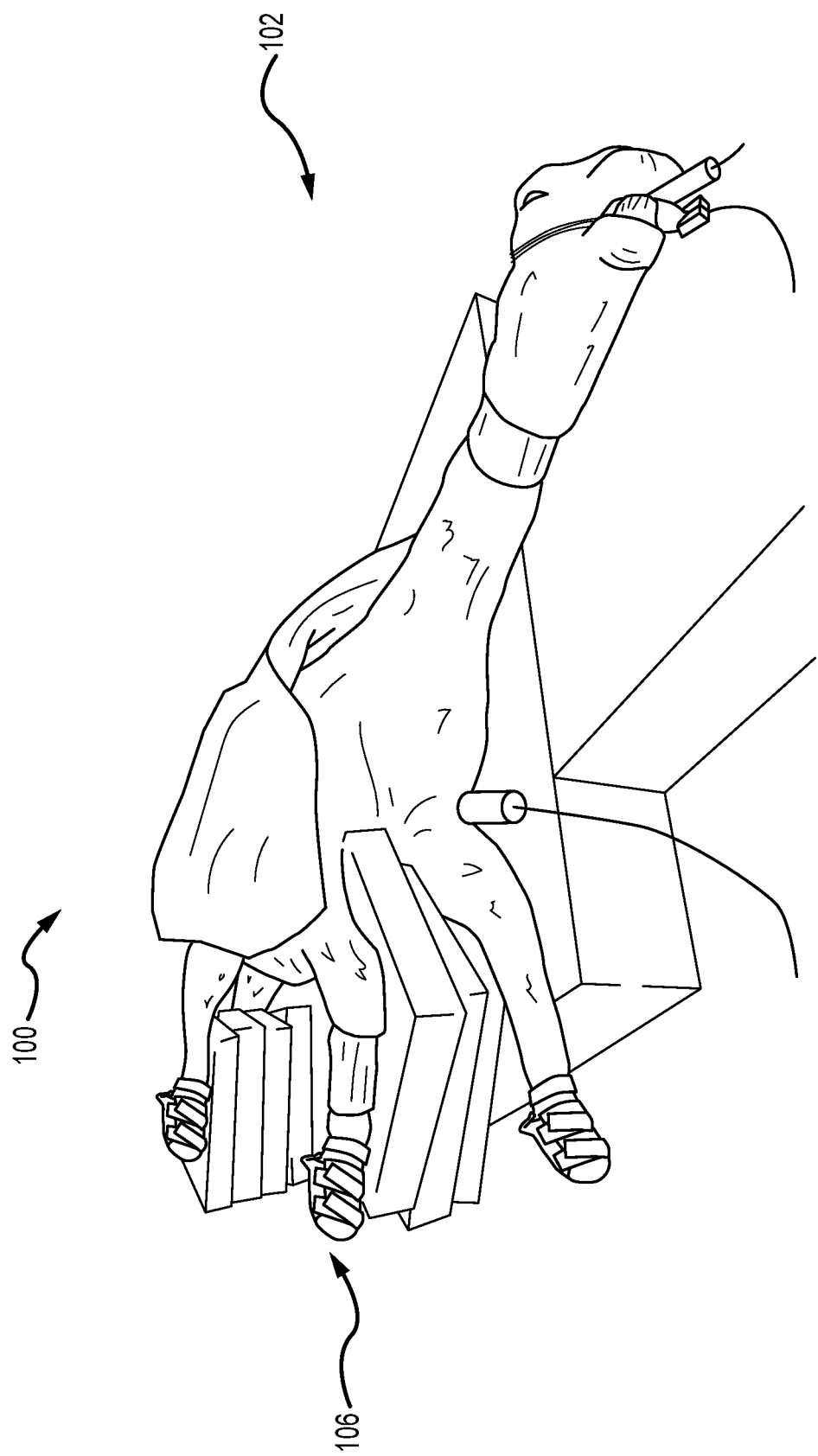
FIG. 7B shows an example equine patient wearing a set of the boots during a veterinary procedure.

To begin a detailed description of an example system 100 for regulating body temperature and monitoring vitals of an animal patient 102 while under anesthesia during a veterinary procedure, reference is made to FIG. 1. The animal patient 102 may be any species of animal having one or more feet, such as paws 104. It will be appreciated, however, that the presently disclosed technology may be applicable to other animal species having other forms of feet. Further, the paws 104 may have anatomy in different forms. In one example, the paws 104 have a plurality of toes and a plurality of pads, including a carpal pad and a metacarpal pad.

In one implementation, the system 100 includes one or more boots 106, each for receiving one of the paws 104. Each of the boots 106 insulates the corresponding paw 104 during the veterinary procedure, thereby regulating the body temperature of the animal patient 102 to increase a positive outcome by reducing the risk of adverse health conditions associated with heat dissipation, such as hypothermia. For example, the animal patient 102 may be unable to regulate its body temperature, due to its anatomy, while under anesthesia, which may cause a drastic drop in body temperature as heat escapes through the pads of the paws 104. In one implementation, each of the boots 106 is held in tension against the paw 104 to optimize a thermal environment of the boot 106. As such, the boots 106 generate a thermal environment that prevents dissipation of body heat through the paws 104.

In addition to regulating body temperature of the animal patient 102, the boots 106 facilitate monitoring of one or more vitals of the animal patient 102 during the veterinary procedure. In one implementation, one or more of the boots 106 includes a sensor set 108 of at least one electrode or other sensor. For example, the electrodes may be electrocardiography (ECG) sensors adapted to capture cardiac data from the animal patient 102 through the paws 104. Each of the electrodes in the sensor set 108 is configured to capture patient vitals data from the animal patient 102 and communicate the data to at least one medical device 110. The boot 106 may be adapted to position the sensor set 108 at an appropriate location on the paw 104 for capturing patient vitals. For example, the boot 106 may position one or more electrodes in the sensor set 108 in contact with the metacarpal pad of the paw 104 to capture cardiac data for the animal patient 102. The sensor set 108 communicates the cardiac data to the medical device(s) 110, which may include an ECG monitor.

Data and/or instructions may be communicated between the sensor set 108 and the medical device(s) 110 via a wired or wireless connection. In one implementation, each of the electrodes in the sensor set 108 is connected to the medical device(s) 110 via one or more corresponding leads 112. A proximal end of each of the leads 112 may connect to the medical device(s) 110, and a distal end of each of the leads 112 may connect to the electrodes in the sensor set 108 in various manners. For example, the electrodes may be button electrodes to which the distal end of the lead 112 snaps. In addition or alternative to the ECG monitor, the medical device(s) 110 may include a blood pressure monitor, a heart rate monitor, a speaker, a display, and/or other monitors, computing devices, and controllers.

The sensor set 108 may be used alone or in conjunction with other components to monitor vitals of the animal patient 102. In one implementation, a Doppler crystal is insertable into the boot 106 and held in position between the metacarpal pad of the paw 104 and one or more of the electrodes in the sensor set 108. The sensor set 108 and the Doppler crystal may capture a pulse of the animal patient 102, which may be communicated to the medical device(s) 110 for output as an audible signal via a speaker. Further, the sensor set 108 and the Doppler crystal may capture a blood pressure of the animal patient 102 and communicate those values to the medical device(s) 110 for presentation. A sphygmomanometer and blood pressure cuff may be used to supplement these values.

The electrodes in the sensor set 108 may be made from a material adapted for capturing and communicating electrical signals while remaining in sit during a Medical Resonance Imaging (MRI) scan. More particularly, while a variety of materials, such as metals, may be used to form electrodes to capture and communicate patient vitals, these materials often generate interference during an MRI scan or are displaced by the magnetic field of the MRI machine. As such, the electrodes in the sensor set 108 may be made from an electrically conducting material that may remain in place during an MRI scan, such as copper or other MRI compatible materials.

In one implementation, the boot 106 is made from a thin, lightweight, flexible material adapted for use by the animal patient 102 in a resting position, for example, while under anesthesia. To enhance the thermal environment of the boot 106, the material may be an insulating, non-absorbent material, such as silicone. The material may further be adapted to permit reuse of the boots 106 while ensuring a sterile environment during the veterinary procedure. More particularly, in one implementation, the material may have a heat resistance that permits exposure to temperatures up to approximately 450 degrees Fahrenheit through autoclaving and/or other sterilization procedures. As such, the boots 106 may be cleaned for reuse, even after potential exposure to bacteria and/or viruses, including MRSA, MRSP, and/or the like.

For a detailed description of an example of the boot 106, reference is made to FIGS. 2-7. In one implementation, the boot 106 includes a base 114 having an interior surface 117 and an exterior surface 118. An opening 116 may be defined in the base 114 through which a corresponding electrode 120 of the sensor set 108 extends. The electrode 120 may be an ECG sensor adapted to engage the lead 112 for communication with the medical device 110, such as an ECG monitor.

A thermal insulator 122 extends from the base 114 forming a housing 124. In one implementation, the housing 124 defines an internal cavity 126 into which the paw 104 is receivable via a housing opening 128. The thermal insulator 122 may extend proximally until reaching an edge that together with the base 114 defines the housing opening 128. In one implementation, the base 114 extends proximally beyond the edge of the thermal insulator 122. Once the paw 104 is received within the internal cavity 126, the housing 124 is held in tension against the paw 104, and a thermal environment for the paw 104 is generated. The thermal environment within the internal cavity 126 prevents the dissipation of body heat of the animal patient 102 via the paws 104, thereby regulating the body temperature of the animal patient 102 while under anesthesia during a veterinary procedure.

In one implementation, the housing 124 is held in tension against the paw 104 with a strap set 130 of one or more straps. The tension may be adjustable using the strap set 130. The strap set 130 may include any number of straps depending on the anatomy of the paw 104. In one implementation, the strap set 130 includes a first strap 132 disposed relative and applying tension to a first portion of the paw 104 and a second strap 134 disposed relative and applying tension to a second portion of the paw 104. The strap set 130 may further include a third strap 136 disposed relative and applying tension to a third portion of the paw 104. The first portion may include an area of the paw 104 disposed between the carpal pad and a metacarpal pad. The second portion may include at least a portion of the metacarpal pad. Finally, the third portion may include the toes of the paw 104. As such, the first strap 132 may be a carpal strap, the second strap 134 may be a metacarpal strap, and the third strap may be a digital strap. In one implementation, the straps 132-136 are generally vertically oriented and disposed adjacent a front portion of the paw 104.

In one implementation, each of the straps in the strap set 130 extends between a first side 138 of the housing 124 and a second side 140 of the housing 124. Each of the straps in the strap set 130 may be removably connected at the first and second sides 138, 140. Alternatively, each of the straps in the strap set 130 may be permanently fixed to the first and second sides 138, 140. In another implementation, each of the straps in the strap set 130 is permanently fixed to one of the sides 138, 140 and removably connected to the other side. The strap set 130 may be integral with the housing 124, separate from the housing 124, connected with the housing 124, extend about the housing 124, and/or otherwise be adapted to apply an adjustable tension of the housing 124 against the paw 104 to generate the thermal environment within the internal cavity 126. The tension further holds the electrode 120 in a position against a portion of the paw 104, such as on or near the metacarpal pad, for capturing patient vital data.

To adjust each of the straps in the strap set 130 and thereby adjust the tension of the housing 124 against the paw 104, in one implementation, each of the straps includes a first connecting surface 142 connectable to a second connecting surface 144. The first and second connecting surfaces 142, 144 may comprise paired hook and loop fasteners or similar connection mechanisms. Further, the first and second connecting surfaces 142, 144 may be disposed on corresponding portions of each of the straps in the strap set 130. Alternatively, the first connecting surface 142 may be disposed on each of the straps in the strap set 130 and the second connecting surface 144 may be disposed on the housing 124. Other connection arrangements are further contemplated.

For example, in one implementation, each of the straps in the strap set 130 extends from the first side 138 of the housing 124 and loops through a corresponding buckle 146 disposed at the second side 140 of the housing 124. After looping through the buckle 146, the first connecting surface 142 of the strap is disposed relative to the second connecting surface 144 and connected thereto. Alternatively or additionally, the first side 138 may include buckles 146 through which the straps permanently or removable loop through for engagement. Each of the buckles 146 may be integral with, separate from, or otherwise connected to the housing 124. In one implementation, the housing 124 includes a lip disposed on the first side 138 and/or the second side 140 with one or more buckles 146 defined as openings in the lips through which the straps in the strap set 130 loop.

In one implementation, the internal cavity 126 is adapted to receive a Doppler crystal on the inside surface 116 of the base 114 between the electrode 120 and a portion of the paw 104, such as on or near the metacarpal pad. The housing 124 holds the Doppler crystal in position until removed. The Doppler crystal may be connected to one of the medical devices 110 via a Doppler crystal cable 148. Imaging gel, such as ultrasound gel and/or Doppler gel, may be applied onto the inside surface 116 and/or onto the Doppler crystal to facilitate monitoring of patient vitals using the electrode 120. By retaining the imaging gel within the internal cavity 126 of the housing 124, a clean environment is provided during the procedure that is easy to clean at the conclusion of the procedure. Further, the paws 104 are easily removable from the internal cavity 126 without harm or irritation to the paws 104.

As such, not only do the boots 106 facilitate regulation of body temperature and vital monitoring for the animal patient 102, the boots 106 are removable from the paws 104 without harm or irritation and permit sterilization for reuse, among other advantages.

Figure 8:
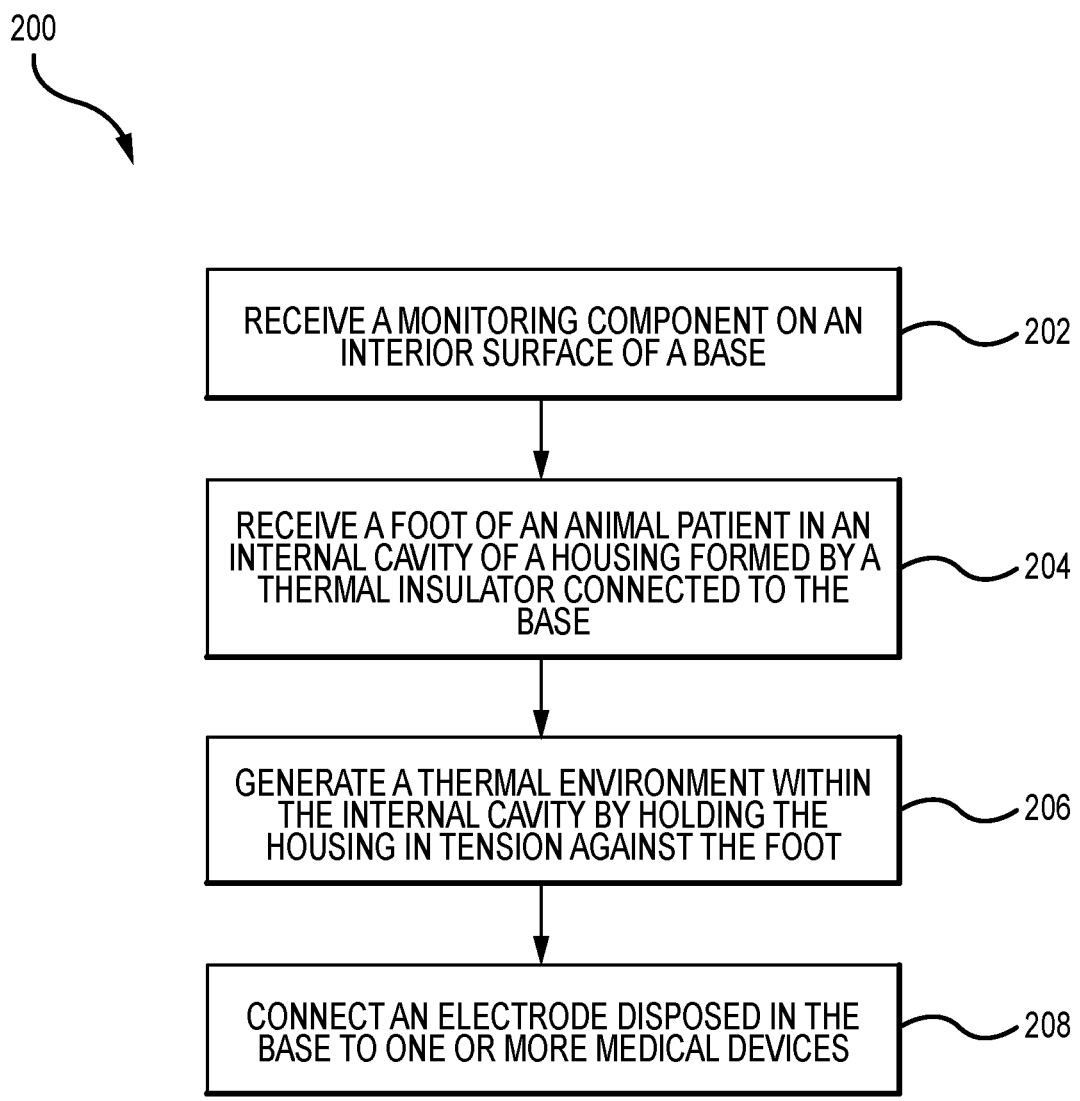
FIG. 8 depicts example operations for regulating a body temperature and monitoring vitals of an animal patient while under anesthesia during a veterinary procedure.

Turning to FIG. 8, example operations 200 for regulating a body temperature and monitoring vitals of an animal patient while under anesthesia during a veterinary procedure are illustrated. In one implementation, an operation 202 receives a monitoring component on an interior surface of a base. The monitoring component may be an imaging gel, such as ultrasound gel or Doppler gel, and/or a Doppler crystal. In one implementation, the monitoring component includes Doppler gel applied to a Doppler crystal. The operation 202 may receive the monitoring component on the interior surface relative to an electrode disposed in the base.

In one implementation, an operation 204 receives a foot, such as a paw, of an animal patient in an internal cavity of a housing formed by a thermal insulator connected to the base. The operation 204 may receive the foot into the internal cavity via a housing opening for example via a sliding movement. In one implementation, the operation 204 orients the foot, such that the monitoring component is disposed between a portion of the foot and the interior surface. In another implementation, the operation 204 orients the foot, such that the portion of the foot is positioned against the electrode. The portion of the foot may be on or near a metacarpal pad of a paw, for example, where the animal patient is a canine or feline patient.

An operation 206 generates a thermal environment within the internal cavity by holding the housing in tension against the foot. In one implementation, the housing is held in tension using a strap set having one or more straps. Additionally or alternatively, the housing may be elastic, have an inward bias, or otherwise be made from a material that automatically provides an inward tension. The thermal environment prevents or reduces heat dissipation of the animal patient via the foot, thereby facilitating regulation of a body temperature of the animal patient.

An operation 208 connects the electrode disposed in the base to one or more medical devices to monitor vitals of the animal patient during the veterinary procedure. In one implementation, the one or more medical devices includes an ECG machine, and the electrode captures cardiac data from the animal patient and communicates the data to the ECG machine for monitoring cardiac vitals of the patient, including heart rate, blood pressure, and/or the like.

It will be appreciated that the boots 106 may be adapted for use with various species of animal patients having different anatomy of feet. The species may include, without limitation, canines, felines, avian, bovine, equine, swine, reptiles, rodents, rabbits, and/or the like. Some examples of the boot 106 adapted for these species are illustrated in FIGS. 9A-11.

Figure 9A:
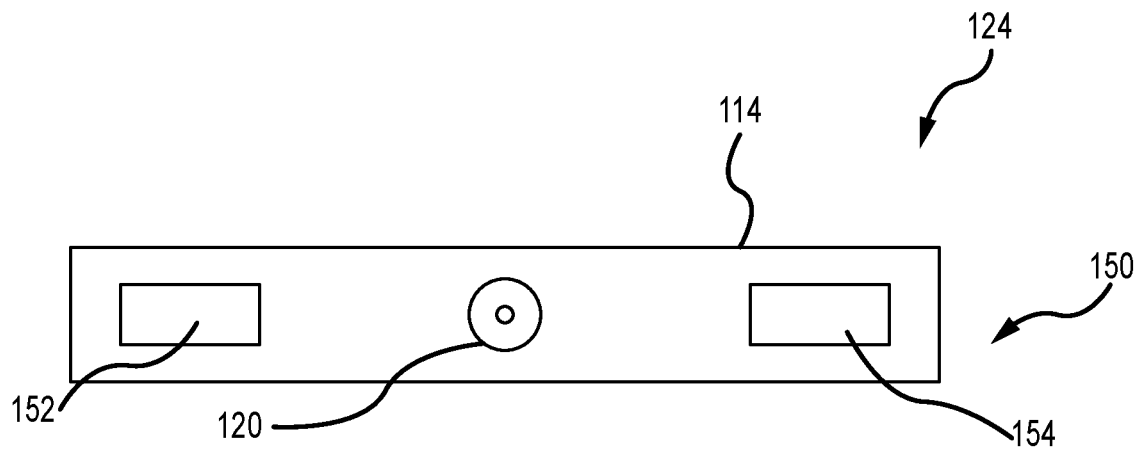
FIGS. 9A-9B illustrate an example of the system for use with an avian patient.
Figure 9B:
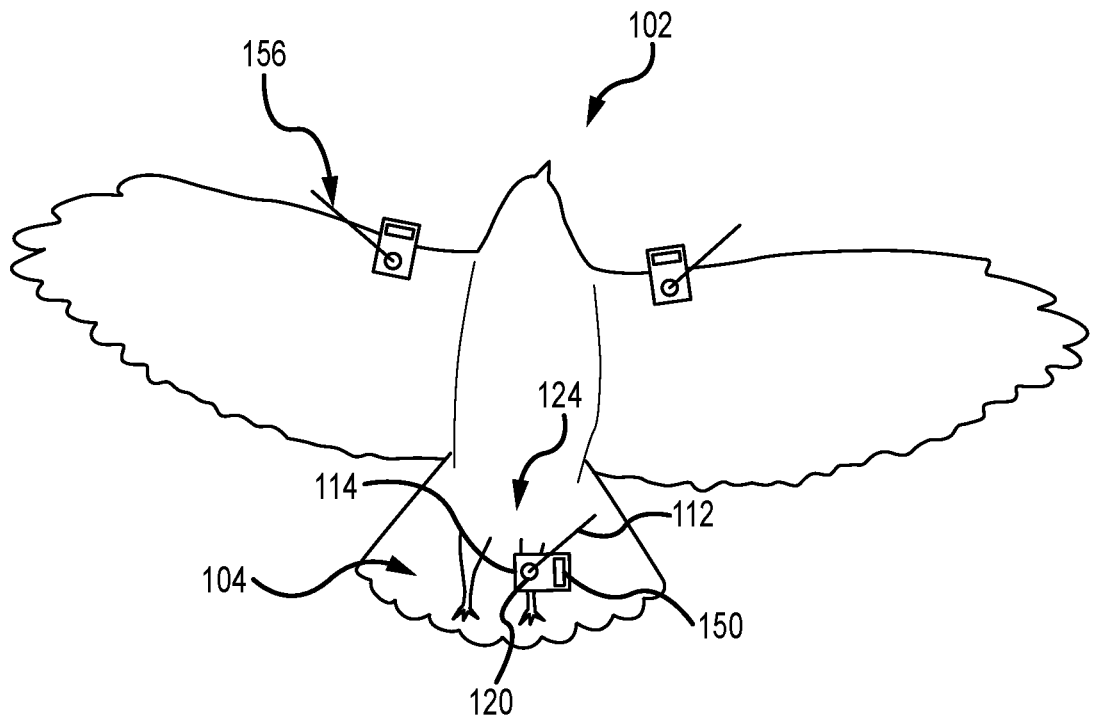

Turning to FIGS. 9A-9B, in one implementation, the housing 124 includes the base 114 with an elongated body extending between a first end and a second end. The base 114 includes the electrode 120, which may be an ECG sensor, and a magnet set 150 having one or more magnets. In one implementation, the magnet set 150 includes a first magnet 152 disposed at the first side and a second magnet 154 disposed at the second side of the base 114. The magnets 152-154 attract each other to hold the housing in tension on the foot 104 of the animal patient 102, in this case, a bird. One or more wing implementations 156 may include similar features and be adapted to capture vitals of the animal patient 102 for monitoring.

Figure 10:
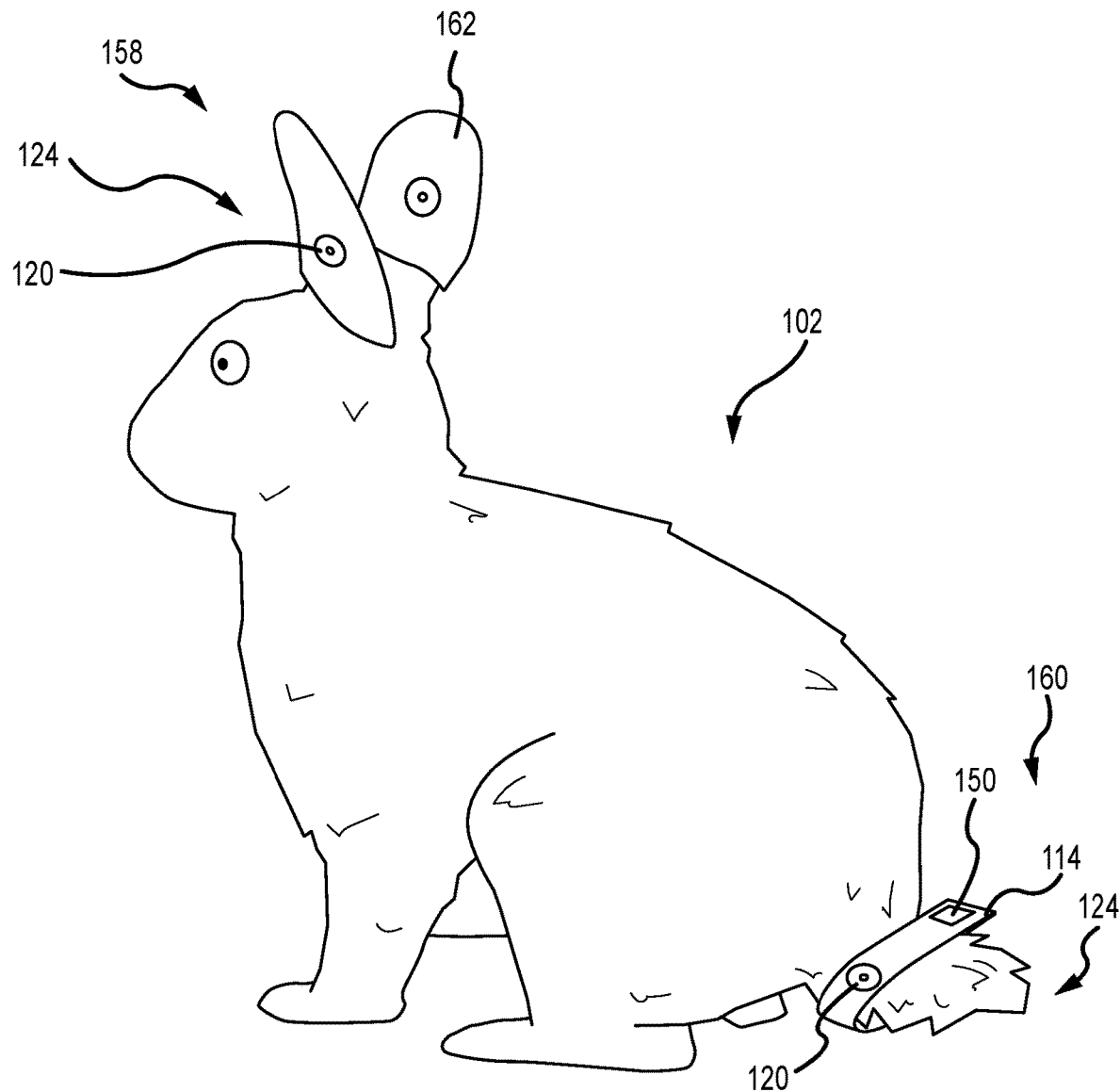
FIG. 10 shows an example of the system for use with a rabbit patient.

FIG. 10 illustrates an ear implementation 158 and a tail implementation 160, which may be used with animal patients 102, such as rabbits or rodents. The ear implementation 158 includes the housing 124 comprising a mesh body 162 (e.g., a silicone mesh) that contains the electrode 120, which may be an ECG sensor. The tail implementation 160 may include similar features to the wing implementation 156 and be adapted to capture vitals of the animal patient 102 for monitoring.

Figure 11:
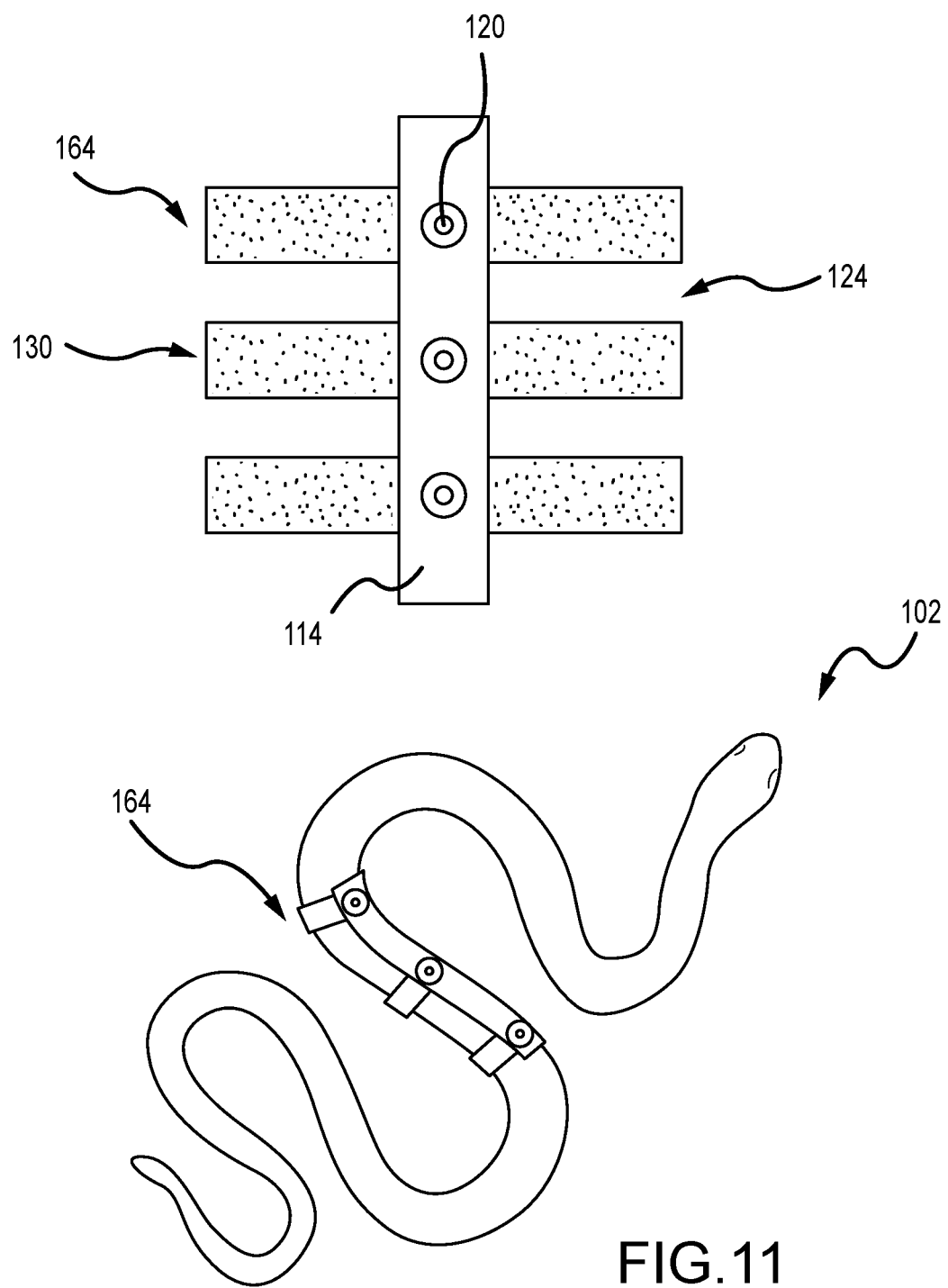
FIG. 11 illustrates an example of the system for use with a reptile patient.

FIG. 11 shows a body implementation 164, which may be used with animal patients 102, such as snakes. Here, the housing 124 may include the base 114 having one or more of the electrodes 120, which may be ECG sensors. The base 114 may be held in tension against the body of the snake with the strap set 130 of one or more straps (e.g., three).

Based upon design preferences, it is understood that the specific order or hierarchy of steps in the methods described herein can be rearranged while remaining within the disclosed subject matter. Any accompanying method claims present elements of the various steps in a sample order and are not necessarily meant to be limited to the specific order or hierarchy presented.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

The above specification, examples, and data provide a complete description of the structure and use of example implementations of the invention. Various modifications and additions can be made to the exemplary implementations discussed without departing from the spirit and scope of the presently disclosed technology. For example, while the implementations described above refer to particular features, the scope of this disclosure also includes implementations having different combinations of features and implementations that do not include all of the described features. Accordingly, the scope of the presently disclosed technology is intended to embrace all such alternatives, modifications, and variations together with all equivalents thereof.

What is claimed is:

1. A device for managing an animal patient during a veterinary procedure, the animal patient having a foot, the device comprising:
    a base having an interior surface and an exterior surface;
    a thermal insulator extending from the base, the thermal insulator forming a housing with the base;
    a strap set having one or more straps extending from a first side of the housing to a second side of the housing, the strap set adapted to apply a tension against the foot of the animal patient, the tension being adjustable using the strap set;
    an opening defined in the base;
    an electrode disposed in the opening, the electrode configured to capture one or more vitals of the animal patient during the veterinary procedure and to communicate the one or more vitals to at least one medical device for monitoring of the animal patient; and
    an internal cavity defined within the housing, the foot of the animal patient receivable into the internal cavity, the thermal insulator regulating the body temperature of the animal patient during the veterinary procedure by retaining heat within the internal cavity.

2. The device of claim 1, wherein a Doppler crystal is receivable on the interior surface of the base between the electrode and a portion of the foot of the animal patient.

3. The device of claim 2, wherein the portion of the foot of the animal patient includes a metacarpal pad of a paw.

4. The device of claim 1, wherein the housing is made of silicone.

5. The device of claim 1, wherein the housing is one or more of antimicrobial, non-absorbent, and flexible.

6. The device of claim 1, wherein the housing has a heat resistance.

7. The device of claim 6, wherein the heat resistance permits exposure to a temperature up to 450 degrees Fahrenheit.

8. The device of claim 6, wherein the heat resistance permits at least one of autoclaving or sterilization of the device.

9. The device of claim 1, wherein the strap set is releasably connected to the housing at the second side.

10. The device of claim 9, wherein the strap set is releasably connected with one or more buckles through which the one or more straps are looped.

11. The device of claim 1, wherein each of the one or more straps includes a first connecting surface engageable to a second connecting surface.

12. The device of claim 11, wherein the first and second connecting surfaces comprise paired hook and loop fasteners.

13. The device of claim 1, wherein the one or more straps include a first strap applying the tension to a first portion of the foot of the animal patient and a second strap applying the tension to a second portion of the foot of the animal patient.

14. The device of claim 13, wherein the first portion of the foot includes an area between a carpal pad and a metacarpal pad of a paw and the second portion of the foot includes at least a portion of the metacarpal pad of the paw.

15. The device of claim 13, wherein the one or more straps further include a third strap applying tension to a third portion of the foot.

16. The device of claim 15, wherein the third portion of the foot includes toes.

17. The device of claim 1, wherein the electrode is connectable to a lead in communication with the at least one medical device.

18. The device of claim 1, wherein the electrode is made of a material adapted for remaining in situ during a Magnetic Resonance Imaging scan.

19. A device for managing an animal patient during a veterinary procedure, the animal patient having a foot, the device comprising:
- a housing formed from a thermal insulator and a base, the housing held in tension against the foot of the animal patient;
- an opening defined in the base;
- an internal cavity defined within the housing, the foot of the animal patient receivable into the internal cavity, the thermal insulator regulating the body temperature of the animal patient during the veterinary procedure by retaining heat within the internal cavity; and
- a sensor disposed in the opening, the sensor configured to capture one or more vitals of the animal patient from the foot during the veterinary procedure.

20. A method for managing an animal patient during a veterinary procedure, the animal patient having a foot, the method comprising:
- receiving a monitoring component on an interior surface of a base relative to an opening defined in the base;
- receiving an electrode in the opening defined in the base;
- receiving the foot of the animal patient in an internal cavity of a housing formed by a thermal insulator connected to the base;
- orienting the monitoring component between a portion of the foot and the electrode using the housing, the electrode capturing one or more vitals of the animal patient from the foot during the veterinary procedure;
- generating a thermal environment within the internal cavity; and
- regulating a body temperature of the animal patient during the veterinary procedure using the thermal environment.

* * * * *